United States Patent [19]

Hottinger et al.

[11] Patent Number: 5,382,438
[45] Date of Patent: Jan. 17, 1995

[54] PREPARATION OF YOGURT WITH LAC(−) L. BULGARICUS

[75] Inventors: Herbert Hottinger, Blonay; Olivier Mignot, Vevey; Beat Mollet, Mollie-Margot, all of Switzerland

[73] Assignee: Nestec S.A., Vevey, Switzerland

[21] Appl. No.: 887,351

[22] Filed: May 21, 1992

[30] Foreign Application Priority Data

Jun. 14, 1991 [EP] European Pat. Off. ............ 91109807

[51] Int. Cl.⁶ ............................................. A23C 9/123
[52] U.S. Cl. ....................................... 426/43; 426/34; 426/583
[58] Field of Search .................... 426/34, 43, 580, 583

[56] References Cited

U.S. PATENT DOCUMENTS

| | | | |
|---|---|---|---|
| 4,425,366 | 1/1984 | Sozzi et al. | 426/43 |
| 4,734,361 | 3/1988 | Murao et al. | 435/34 |

FOREIGN PATENT DOCUMENTS

| | | | |
|---|---|---|---|
| 518096A | 12/1992 | European Pat. Off. | 426/43 |
| 60-256341 | 1/1985 | Japan . | |
| 2-53437 | 8/1990 | Japan . | |
| WO90/05459 | 3/1990 | WIPO . | |

OTHER PUBLICATIONS

Mainzer et al., 91:3662 FSTA DN 91-03-P0104, Pathway engineering of Lactobacillus bulgaricus for improved yogurt (In yogurt: nutritional and health properties, by Chandan, R. C. Conference, New York, USA, 21-23 May 1989, Mclean, Va., USA; National Yogurt Association.

Schmidt, et al., "Expression and Nucleo-tide Sequence of the Lactobacillus bulgaricus δ-Galactosidase Gene Cloned in Escherichia coli," J. of Bacteriology, Feb. 1989, vol. 171, No. 2, pp. 625-635.

Mollet, et al., A δ-galactosidase deletion mutant of Lactobacillus bulgaricus reverts to generate an active enzyme by internal DNA sequence duplication. Mol Gen Genet (1991) 227:17–21.

Mollet, et al., Spontaneous Deletion Formation within the δ-Galactosidase Gene of Lactobacillus bulgaricus. Journal of Bacteriology, vol. 172, No. 10, pp. 5670-5676 (1990).

Amoroso, et al., "Glucose, galactose, fructose and sucrose utilization by Lactobacillus bulgaricus and Streptococcus thermophilus isolated from commercial yoghurt", Milchwissen-schaft, vol. 43, No. 10, 1988 pp. 626-631.

*Primary Examiner*—Donald E. Czaja
*Assistant Examiner*—Curtis E. Sherra
*Attorney, Agent, or Firm*—Vogt & O'Donnell

[57] ABSTRACT

Yogurt is prepared by inoculating and fermenting a milk with a strain of Streptococcus thermophilus and a lac(-) mutant strain of Lactobacillus bulgaricus, the DNA of which has a deletion of at least part of the β-galactosidase gene.

19 Claims, No Drawings

PREPARATION OF YOGURT WITH LAC(−) L. BULGARICUS

BACKGROUND OF THE INVENTION

This invention relates to a yogurt and to a process for its production and also to a mutant of "Lactobacillus bulgaricus" and to a process for its selection.

Yogurt is obtained by fermentation of milk with a combination of strains of "Streptococcus thermophilus" and Lactobacillus bulgaricus and is present in the form of a gel containing the living strains. Yogurt is a fresh product with a limited shelf life, even under refrigeration. Various processes have been proposed with a view to improving its keeping properties and, in particular, reducing the increase in its acidity, in other words its post-acidification, and the appearance of a bitter taste which adversely affect its organoleptic qualities.

Thus, Japanese Patent Application Kakai No.85256341 describes the production of a mild yogurt using a mixed starter in which the numbers of cells/ml of "L. bulgaricus" and "S. thermophilus" are in a preferred ratio of 1:100. Although the reduction in the relative number of "L. bulgaricus" cells does enable the post-acidification of the yogurt during refrigerated storage to be reduced, it can also produce a reduction in the typically yogurt organoleptic character of the product which is due to the work of the two microorganisms in symbiosis.

U.S. Pat. No. 4,425,366 describes the production of a long-life yogurt using a combination of strains of "L. bulgaricus" and "S. thermophilus" in which the "L. bulgaricus" strain shows low proteolytic activity. However, this document also proposes using a relative number of "L. bulgaricus" cells of the order of 1:100.

U.S. Pat. No. 4,734,361 describes the selection of a strain of "L. bulgaricus" sensitive to low temperatures, i.e. having a low activity at a storage temperature of 10° C. and high activity at a fermentation temperature of 43° C. The strain FERM BP-1041 thus selected was derived from the strain ATCC 11842.

Japanese Patent Application Kokai No. 90053437 describes the production of a yogurt using - in combination with a strain of "S. thermophilus" a strain of "L. bulgaricus" selected for its inability (artificial mutant SBT-0218) or its reduced capacity (natural mutant SBT-0220) to ferment lactose. The starting milk thus has to be supplemented with glucose.

International Patent Application No. WO90/05459 proposes the construction of an "L. bulgaricus" sensitive to low temperatures or to low pH values by selective mutation on "E. coli" of a β-galactosidase gene taken from "L. bulgaricus" and intended for reincorporation in "L. bulgaricus".

SUMMARY OF THE INVENTION

The present invention relates to the production of a yogurt of which the organoleptic qualities do not deteriorate in storage and which shows a typical traditional character due to the work of the two microorganisms "S. thermophilus" and "L. bulgaricus" in symbiosis. The present invention also relates to a safe and reproducible process for selecting a mutant of "L. bulgaricus" which, used in combination with at least one strain of "S. thermophilus", enables such a yogurt to be produced.

The yogurt according to the present invention contains:
- 10 to 20% by weight dry matter of an animal and/or vegetable milk,
- $10^6$–$10^{10}$ cells/ml of a mutant of "Lactobacillus bulgaricus" in the DNA of which a fragment containing at least part of the β-galactosidase gene is missing and
- $10^6$–$10^{10}$ cells/ml of "Streptococcus thermophilus".

In the process according to the invention for the production of a yogurt, a milk is fermented with a combination of at least one strain of "Streptococcus thermophilus" and a mutant of "Lactobacillus bulgaricus" the DNA of which contains a deletion of at least part of the β-galactosidase gene.

The mutant of "Lactobacillus bulgaricus" according to the invention therefore has a DNA where a fragment containing at least part of the β-galactosidase gene is missing.

In the process for selecting a mutant of "L. bulgaricus" according to the invention,
- a mother strain of "L. bulgaricus" is screened on an X-gal plate to isolate colonies having a β-galactosidase minus mutation,
- these colonies of mutants are subjected to a stability test in a medium containing lactose as sole energy source,
- the chromosomal DNA of stable mutants is digested with restriction enzymes and is subjected to a test for detecting fragments contained in a region comprising the β-galactosidase strain and
- a mutant having a DNA from which a fragment containing at least part of the β-galactosidase gene is missing is selected.

DETAILED DESCRIPTION OF THE INVENTION

It has been found that it is possible to produce a yogurt in which post-acidification and the appearance of a bitter taste during storage are significantly reduced and of which the organoleptic qualities have a traditional character typical of yogurt due to the work of two microorganisms "S. thermophilus" and "L. bulgaricus" in symbiosis.

More particularly, it has been found that the "bulgaricus" mutant according to the invention has the surprising property of causing only slight post-acidification in storage while actively working in symbiosis with "S. thermophilus" during fermentation. In particular, the respective numbers of cells of these two microorganisms can be in a relatively balanced ratio, more particularly in a ratio of approximately 1:20 to 1:1, both at the beginning of incubation and in the yogurt obtained.

In two preferred embodiments of the yogurt, the process for its production, the mutant and the process for its selection, the missing DNA fragment either contains only part of the β-galactosidase gene or contains at least part of the β-galactosidase gene and extends at least below that gene over at least 1.0 kb.

There is thus a deletion of at least a part of the β-galactosidase gene. The deletion may be within the gene or it may extend from within the gene to at least 1 kb downstream of the gene.

The first of these two preferred embodiments is more particularly intended for use in countries with a temperate or even relatively cold climate. The second of the two preferred embodiments is more particularly intended for use in countries with a relatively hot climate.

The first preferred embodiment is also capable of being used in countries having a relatively hot climate as long as adequate refrigeration means, more particularly a cold chain, are available. Similarly, the second preferred embodiment is also capable of being used in countries having a relatively cold climate without making use of particular refrigeration means so that, in particular, there is no need for a cold chain.

In the first preferred embodiment, the "L. bulgaricus" mutant is apparently incapable on its own of fermenting lactose although, cultured in a milk in symbiosis with "S. thermophilus", it is capable of acidifying this milk almost as well as the mother strain from which it has come. The addition of small quantities of glucose enables the acidification rate and the level of post-acidification in storage to be modulated.

In the second preferred embodiment, the "L. bulgaricus" mutant is apparently incapable on its own of fermenting lactose although, cultured in a milk in symbiosis with "S. thermophilus", it acidifies the milk at a lower rate and to a lower pH value than the mother strain from which it has come. The addition of a small quantity of glucose enables the acidification rate to be slightly accelerated and the pH value reached to be slightly lowered virtually without presenting any problems of post-acidification.

In each of these two preferred embodiments, it is possible to maintain a relatively large number of living cells of each of the microorganisms in the yogurts obtained.

The starting material used to carry out the process according to the invention for the production of a yogurt may be an animal and/or vegetable, fresh or reconstituted, skimmed, semi-skimmed or whole, pasteurized milk having a dry matter content of 10 to 20% by weight. This milk is preferably inoculated with 0.2 to 5% and, more preferably, with 0.5 to 3% by volume of a culture containing $10^6$–$10^{10}$ and preferably $10^8$–$10^9$ cells/ml of the "Lactobacillus bulgaricus" mutant and 1 to 5% and preferably 2 to 4% by volume of a culture containing $10^6$–$10^{10}$ and preferably $10^8$–$10^9$ cells/ml of "Streptococcus thermophilus".

The milk may be fermented for 2.5 to 15 h at 35 to 48° C. The pH value reached during fermentation or acidification may vary between about 4.3 and 4.8 in the first embodiment, i.e. in the embodiment where the missing DNA fragment of "L. bulgaricus" only contains at least part of the β-galactosidase gene. This pH may be reduced by approximately 0.1 to 0.5 unit by addition of approximately 0.2 to 2% by weight glucose to the starting milk.

The pH reached during fermentation or acidification may vary between about 4.5 and 5.0 in the second embodiment, i.e. the embodiment in which the missing DNA fragment of "L. bulgaricus" contains at least part of the β-galactosidase gene and extends at least below that gene over at least 1.0 kb. The pH value may be reduced by approximately 0.05 to 0.3 unit by addition of approximately 0.2 to 2% by weight glucose to the starting milk.

It is possible in this way to obtain a yogurt containing respective numbers of cells/ml of the mutant of "L. bulgaricus" and "S. thermophilus" comparable with the numbers of cells/ml present in the cultures used for incubation. The ratios between these respective numbers are preferably between about 1:20 and 1:7 or even between 1:20 and 1:4 in the first embodiment and between about 1:10 and 1:4 or even between 1:10 and 1:1 in the second embodiment.

Accordingly, the yogurt shows organoleptic qualities having the typical character of traditional yogurt due to the use in symbiosis of "L. bulgaricus" and "S. thermophilus". It may be kept for several weeks under refrigeration or even at ambient temperature for the second embodiment without the pH value falling by more than about 0.05–0.5 unit, without the appearance of a bitter taste and without the number of living cells which it contains showing significant variations.

To carry out the process according to the invention for selecting a mutant of "L. bulgaricus", a strain used commercially so that it has all the qualities required for the production of a good traditional commercial yogurt is preferably used as the mother strain.

This mother strain may be screened on an X-gal plate, for example as described by B. Mollet et al., Journal of Bacteriology 172, 5670–5676 (1990) with reference to J. H. Miller (1972). It is possible in this way to isolate colonies having a β-galactosidase minus mutation, i.e. mutants which are incapable of fermenting lactose due to a malfunction of the β-galactosidase enzyme by means of which "L. bulgaricus" should normally hydrolyze the lactose into glucose and galactose before being able to consume the glucose.

These colonies of mutants may be subjected to a stability test by culturing them in a medium containing lactose as sole energy source, such as cow's milk for example, in order to eliminate the mutants capable of returning spontaneously to the original β-galactosidase plus state.

The chromosomal DNA may be extracted from the stable mutants, for example by the method described by M. Delley et al., Appl. Environ. Microbiol. 56, 1967–70 (1990). The DNA may be digested with restriction enzymes such as, for example, BamHI, EcoRI, HindIII, SalI and TaqI.

The digested DNA is then subjected to a test for detecting fragments contained in a region comprising the β-galactosidase gene. To this end, the DNA fragments thus obtained may be separated on agarose gel and placed on a transfer membrane for screening genes by hybridization and hybridization may be carried out with a DNA probe carrying the β-galactosidase gene, for example by Southern's blotting method (E. Southern, J. Mol. Biol. 98, 503–517, 1975). The DNA probe used may be a fragment SalI-BamHI of the plasmid pMZ2 (B. Mollet et al., J. Bacteriol. 172, 5670–5676, 1990) which may be labelled with $^{32}$p which has a length of 4.3 kb and which contains all the β-galactosidase gene for example.

The detection test may also be carried out, for example, by the PCR method with specific primers (PCR is the abbreviation for polymerase chain reaction; cf. Saiki et al., Science 230, 1350–1354, 1985 and Saiki et al., Science 239, 487–491, 1988).

A mutant having a DNA in which a fragment containing at least part of the β-galactosidase gene is missing may then be selected. It has been found that mutants such as these of a commercial mother strain could advantageously be used in symbiosis with "S. thermophilus" for the production of the yogurts according to the invention.

More particularly, it has been found that mutants such as these having a DNA where a fragment containing only part of the β-galactosidase gene is missing (this fragment may have a length between a few base pairs and almost the entire length of the β-galactosidase gene) are particularly suitable for the production of a yogurt capable of keeping for long periods under refrigeration in countries with a temperate or relatively cold climate. Among various selected mutants of this type, one was lodged by way of example under the Budapest Treaty on 29.03.91 at the Collection Nationale de Cultures de Microorganismes (CNCM), Institut Pasteur, 28 rue du Dr. Roux, 7524 Paris Cedex 15, France, where it was given the number CNCM I-1068.

Details of the morphology and the properties of this strain CNCM I-1068 are given in the following:

Morphology:
Gram-positive microorganism, negative catalase and optional anaerobe.
Straight bacilli without flagella or formation of spores.
Fermentation of sugars:
Production of acid from
D-glucose
D-fructose
D-mannose
Others:
No production of acid from lactose (no functional β-galactosidase enzyme).

More particularly, it has also been found that mutants of the type in question having a DNA where a fragment containing at least part of the β-galactosidase gene and extending at least below that gene over at least 1.0 kb is missing are particularly suitable for the production of a yogurt capable of keeping for long periods under refrigeration in countries with a relatively hot climate. Among the various selected mutants of this type, one was lodged by way of example under the Budapest Treaty on 29.03.91 at the Collection Nationale de Cultures de Microorganismes (CNCM), Institut Pasteur, 28 rue du Dr. Roux, 7524 Paris Cedex 15, France, where it was given the number CNCM I-1067.

Details of the morphology and the properties of this strain CNCM I-1067 are given in the following:

Morphology:
Gram-positive microorganism, negative catalase and optional anaerobe.
Straight bacilli without flagella or formation of spores.
Fermentation of sugars:
Production of acid from
D-glucose
D-fructose
D-mannose
Others:
No production of acid from lactose (no functional β-galactosidase enzyme).

EXAMPLES

The products and processes according to the invention are illustrated in the following Examples in which percentages are by weight, unless otherwise indicated.

Example 1

5 litres MRS culture medium are sterilized for 15 minutes at 121° C. and then inoculated with 5% by volume of an active culture of the "Lactobacillus bulgaricus" strain CNCM I-1068 containing approximately $10^9$ cells/mi. After incubation for 8 h at 41° C., a starter containing 4.5–$10^8$ cells/ml is obtained.

5 litres reconstituted skimmed milk having a dry matter content of 10%, to which 0.1% yeast extract has been added, are sterilized for 15 minutes at 121° C. and inoculated with 2% of an active culture of commercial thickening "Streptococcus thermophilus" containing approximately $10^9$ cells/mi. After incubation for 4 h at 41° C., a starter containing 4.5·$10^8$ cells/ml is obtained.

One batch of whole milk containing 3.7% fats strengthened with 2.5% skimmed milk powder and pasteurized for 30 mins. at 90° C. is then inoculated with 2% by volume of the starter of "L. bulgaricus" I-1068 and 3% by volume of the starter of thickening "S. thermophilus". The inoculated milk is stirred, poured into pots and incubated for 4 h at 41° C.

The yogurt obtained has a good firm and smooth texture and an agreeable mild flavour typical of this type of product. It has a pH of 4.53 and contains 4.6·$10^7$ cells/ml of "L. bulgaricus" I-1068 and 6.8·$10^8$ cells/ml of "S. thermophilus".

This yogurt is subjected to a storage test at 4° C. and 12° C. In this test, the pH is measured and the product is tasted after storage for 1, 7, 14 and 24 d (days). The results are shown in Table 1 below.

Example 2

The procedure is as described in Example 1, except that the "L. bulgaricus" strain CNCM I-1067 is used instead of the strain CNCM I-1068.

The "L. bulgaricus" starter obtained contains 5.2·$10^8$ cells/mi.

The yogurt obtained has a pH of 4.55 after incubation for 8h30 at 41° C. It contains 5.6·$10^7$ cells/ml of "L. bulgaricus" CNCM I-1067 and 5.5·$10^8$ cells/ml of "S. thermophilus". It has a good texture and an agreeable flavour comparable with those of the yogurt obtained in Example 1.

This yogurt is subjected to the storage test described in Example 1. The results are set out in Table 1 below.

Comparison Example i)

By way of comparison, Example 1 is repeated replacing the two mutants I-1067 and I-1068 by their mother strain which is a strain used industrially for the production of yogurts.

The comparison yogurt (i) obtained has a pH of 4.53 after incubation for 3h30 at 41° C. It contains 2.9·$10^7$ cells/ml of "L. bulgaricus" and 4.9·$10^8$ cells/ml "S. thermophilus". It has a good texture and an agreeable mild flavour.

This comparison yogurt (i) is subjected to the storage test described in Example 1. The results are set out in Table 1 below.

TABLE 1

| Ex. No. (CNCM No.) | Storage time (d) | Storage at 4° C. pH | Storage at 4° C. Tasting | Storage at 12° C. pH | Storage at 12° C. Tasting |
|---|---|---|---|---|---|
| 1 (I-1068) | 1 | 4.53 | Good, mild | 4.53 | Good, mild |
|  | 7 | 4.41 | Good, mild | 4.20 | Good, aromatic |
|  | 14 | 4.30 | Good, aromatic | 4.13 | Good, aromatic |
|  | 24 | 4.22 | Good, aromatic | 4.06 | Good, aromatic |
| 2 (I-1067) | 1 | 4.55 | Good, mild | 4.55 | Good, aromatic |
|  | 7 | 4.48 | Good, mild | 4.35 | Good, aromatic |
|  | 14 | 4.46 | Mild, aromatic | 4.22 | Good, aromatic |
|  | 24 | 4.42 | Mild, aromatic | 4.20 | Good, aromatic |

TABLE 1-continued

| Ex. No. (CNCM No.) | Storage time (d) | Storage at 4° C. pH | Storage at 4° C. Tasting | Storage at 12° C. pH | Storage at 12° C. Tasting |
| --- | --- | --- | --- | --- | --- |
| Comparison i) (yogurt i) | 1 | 4.53 | Good, mild | 4.53 | Good, mild |
|  | 7 | 4.27 | Slightly acidic | 4.18 | Acidic |
|  | 14 | 4.18 | Slightly bitter | 3.97 | Bitter |
|  | 24 | 4.16 | Slightly bitter | 3.92 | Very acidic, bitter |

These results show that the two yogurts of Examples 1 and 2 are highly stable in storage, their post-acidification being far less rapid than that of the comparison yogurt. The post-acidification of the yogurt of Example 2 is even lower than that of the yogurt of Example 1. Finally, in contrast to the comparison yogurt, no appearance of even a slight bitter taste is observed in the yogurts of Examples 1 and. 2.

Examples 3–6

The procedure is as described in Example 1 except that 0.5% glucose is added to the milk of Example 3 and 1% glucose is added to the milk of Example 4 before pasteurization.

Similarly, the procedure of Example 2 is repeated except that 0.5% glucose is added to the milk of Example 5 and 1% glucose is added to the milk of Example 6.

The inoculated milk is incubated for 3h40 at 41° C. to a pH of 4.55 in Example 3, for 3h40 to a pH of 4.53 in Example 4 and for 8 h to a pH of 4.63 in Examples 5 and 6.

The yogurts thus obtained have a good texture and an agreeable flavour. Their respective contents of "L. bulgaricus" and "S. thermophilus", expressed as the number of active cells per ml, are $4.7 \cdot 10^7$ (I-1068) and $6.4 \cdot 10^8$, $7 \cdot 10^7$ (I-1068) and $9.0 \cdot 10^8$, $7.8 \cdot 10^7$ (I-1067) and $7.5 \cdot 10^8$ and $7.9 \cdot 10^7$ (I-1067) and $5.7 \cdot 10^8$ for Examples 4, 5, 6 and 7, respectively.

All these yogurts are subjected to the storage test described in Example 1. The results obtained are set out in Table 2 below:

TABLE 2

| Ex. No. (CNCM No.) | Storage time (d) | Storage at 4° C. pH | Storage at 4° C. Tasting | Storage at 12° C. pH | Storage at 12° C. Tasting |
| --- | --- | --- | --- | --- | --- |
| 3 (I-1068) | 1 | 4.55 | Good, mild | 4.55 | Good, mild |
|  | 7 | 4.36 | Good, aromatic | 4.07 | Good, acidic |
|  | 14 | 4.30 | Good, aromatic | 4.01 | Good, acidic |
|  | 24 | 4.25 | Good, aromatic | 3.94 | Good, acidic |
| 4 (I-1068) | 1 | 4.53 | Good, mild | 4.53 | Good, mild |
|  | 7 | 4.24 | Good, aromatic | 4.00 | Good, acidic |
|  | 14 | 4.15 | Good, aromatic | 3.93 | Very acidic |
|  | 24 | 4.08 | Good, aromatic | 3.84 | Very acidic |
| 5 (I-1067) | 1 | 4.63 | Good, mild | 4.63 | Good, mild |
|  | 7 | 4.42 | Good, aromatic | 4.30 | Aromatic |
|  | 14 | 4.42 | Good, aromatic | 4.19 | Aromatic |
|  | 24 | 4.40 | Good, aromatic | 4.16 | Aromatic |
| 6 (I-1067) | 1 | 4.63 | Good, mild | 4.63 | Good, mild |
|  | 7 | 4.42 | Good, aromatic | 4.31 | Aromatic |
|  | 14 | 4.42 | Good, aromatic | 4.22 | Aromatic |
|  | 24 | 4.40 | Good, aromatic | 4.15 | Aromatic |

These results show that the degree of post-acidification of the yogurt may be modulated by addition of glucose to the milk when the "L. bulgaricus" mutant used is of the type in which the missing DNA fragment contains only part of the β-galactosidase gene (Examples 3 and 4, "L. bulgaricus" CNCM I-1068). This more or less reduced post-acidification means that a mutant such as this is more particularly intended for use in the production of yogurts in countries with a temperate or relatively cold climate.

By contrast, the degree of post-acidification of the yogurt is hardly affected by addition of glucose to the milk when the "L. bulgaricus" mutant used is of the type in which the missing DNA fragment contains at least part of the β-galactosidase gene and extends at least below that gene over at least 1.0 kb (Examples 5 and 6, "L. bulgaricus" CNCM I-1067). This absence of effect of glucose on postacidification enables a mutant of this type to be used, for example, for the production of sweetened flavoured yogurts. In addition, the greatly reduced post-acidification, even at 12° C., predestines a mutant such as this to be used in particular for the production of yogurts in countries with a relatively hot climate.

Example 7

Two starters similar to those of Example 2 are prepared, one containing $4.3 \cdot 10^8$ cells/ml of "L. bulgaricus" CNCM I-1067 and the other containing $6 \cdot 10^8$ cells/ml thickening "S. thermophilus".

A partly skimmed milk containing 2.8% fats strengthened with 5% skimmed milk powder and pasteurized for 30 minutes at 90° C. is inoculated with 2% by volume of the "L. bulgaricus" starter and 3.5% by volume of the starter of thickening "S. thermophilus". After incubation for 8 hours at 41° C., the yogurt obtained is cooled and stirred before being put into pots. The stirred yogurt obtained has a pH of 4.62, a good creamy texture and an agreeable flavour and contains $6.4 \cdot 10^8$ cells/ml of "L. bulgaricus" CNCM I-1067 and $4.5 \cdot 10^8$ cells/ml thickening "S. thermophilus".

This yogurt is subjected to the storage test described in Example 1. The results of the test are set out in Table 3 below.

Comparison Example ii)

The procedure is as described in Example 7, except that the "L. bulgaricus" starter is not prepared with the strain CNCM I-1067, but with one of the strains of low proteolytic activity according to U.S. Pat. No. 4,425,366.

The same milk is then inoculated under the same conditions as in Example 7. After incubation for 8h30 at 41° C., a yogurt of the stirred type is again obtained. It has a pH of 4.63, a creamy texture and an agreeable flavour and contains $1.6 \cdot 10^7$ cells/ml of "L. bulgaricus" and $2.6 \cdot 10^8$ cells/ml of "S. thermophilus".

This comparison yogurt is subjected to the storage test described in Example 1. The results obtained are set out in Table 3 below.

TABLE 3

| Ex. No. (CNCM No.) | Storage time (d) | Storage at 4° C. | | Storage at 12° C. | |
|---|---|---|---|---|---|
| | | pH | Tasting | pH | Tasting |
| 7 (I-1067) | 1 | 4.62 | Good, mild | 4.62 | Good, mild |
| | 7 | 4.53 | Good, mild | 4.46 | Aromatic |
| | 14 | 4.48 | Slightly aromatic | 4.29 | Aromatic |
| | 24 | 4.47 | Slightly aromatic | 4.24 | Aromatic |
| Comparison ii) (yogurt ii) | 1 | 4.63 | Mild | 4.63 | Good, mild |
| | 7 | 4.54 | Mild | 4.39 | Good, mild |
| | 14 | 4.47 | Mild | 4.25 | Slightly acidic |
| | 24 | 4.39 | Slightly aromatic | 4.19 | Slightly acidic |

These results show that the strain CNCM I-1067 can advantageously replace one of the strains of U.S. Pat. No. 4,425,366 in the production of a long-life yogurt because, for comparable post-acidification, it enables a more aromatic yogurt containing a larger relative number of "L. bulgaricus" cells to be obtained.

Example 8–11 (selection)

The selection process according to the invention is used as described above to select a mutant of "L. bulgaricus" from four different commercial mother strains of which two have texturing, i.e. thickening, properties. Various mutants having a DNA in which a fragment containing only part of the β-galactosidase gene is missing are thus selected.

Of these mutants, four, namely one for each different mother strain, were lodged by way of example under the Budapest Treaty on 02.04.92 at the Collection Nationale de Cultures de Microorganismes (CNCM), Institut Pasteur, 28 rue du Dr. Roux, 7524 Paris Cedex 15, France, where they were given the numbers CNCM I-1191, I-1193, I-1196 and I-1198.

Details of the morphology and the properties of these strains are given in the following:

Morphology:
Gram-positive microorganisms, negative catalases, optional anaerobes.
Straight bacilli without flagella or spore formation.
Fermentation of sugars:

| | production of acid from: | | | |
|---|---|---|---|---|
| | I-1191 | I-1193 | I-1196 | I-1198 |
| D-Glucose | + | + | + | + |
| D-Fructose | + | + | + | + |
| D-Mannose | + | + | + | + |
| Trehalose | + | − | − | − |

Others:
No production of acid from lactose (no functional β-galactosidase enzyme).
The strains CNCM I-1196 and I-1198 have texturing properties (production of polysaccharides).

Examples 8 and 9 (production of yogurts)

Two starters each containing approx. $10^8$ cells/ml of one of the strains of "L. bulgaricus" CNCM I-1191 and I-1193 and a starter containing approx. $10^9$ cells/ml of a culture of commercial "Streptococcus thermophilus" are prepared.

Two batches of 40 l of fresh milk containing 3.7% fats strengthened with 1.5% skimmed milk powder and pasteurized for 3 mins. at 98° C. are prepared and are each inoculated with 2% by volume of one of the two starters of "L. bulgaricus" CNCM I-1191 and I-1193. The batches are then incubated at 40° C. for 9 h and 4 h 15 mins., respectively.

The yogurts obtained have a firm and smooth texture, a mild and typical flavour, a pH of 4.65 and respective contents, expressed as the number of cells of "L. bulgaricus" and "S. thermophilus" per ml, of $4.5 \cdot 10^6$ (I-1191) and $2.2 \cdot 10^8$ and $2.4 \cdot 10^7$ (I-1193) and $5.5 \cdot 10^8$.

These yogurts are subjected to the storage test described in Example 1. The results are shown in Table 4 below.

Examples 10 and 11 (production of yogurts)

Two starters each containing approx. $10^8$ cells/ml of one of the thickening "L. bulgaricus" strains CNCM I-1196 and I-1198 and a starter containing approx. $10^9$ cells/ml of a commercial "S. thermophilus" culture are prepared.

Two batches of 20 l of milk containing 1.5% fats strengthened with 2.5% skimmed milk powder and pasteurized are prepared and are each inoculated with 2% by volume of one of the two starters of thickening "L. bulgaricus" CNCM I-1196 and I-1198. The two batches are then incubated for 5 h at 40° C.

The yogurts obtained have a creamy texture, a mild and typical flavour, a pH of 4.65 and respective contents, expressed as the number of cells of "L. bulgaricus" and "S. thermophilus" per ml, of $6.0 \cdot 10^6$ (I-1196) and $3.5 \cdot 10^8$ and $1.8 \cdot 10^7$ (I-1198) and $5.0 \cdot 10^7$.

These yogurts are subjected to the storage test described in Example 1. The results are shown in Table 4 below.

TABLE 4

| Ex. No. (CNCM No.) | Storage time (d) | Storage at 4° C. | | Storage at 12° C. | |
|---|---|---|---|---|---|
| | | pH | Tasting | pH | Tasting |
| 8 (I-1191) | 1 | 4.50 | Good, mild | 4.50 | Good, mild |
| | 7 | 4.39 | Good, mild | 4.25 | Good, aromatic |
| | 14 | 4.33 | Good, aromatic | 4.18 | Good, aromatic |
| | 24 | 4.28 | Good, aromatic | 4.05 | Good, aromatic |
| 9 (I-1193) | 1 | 4.44 | Good, mild | 4.44 | Good, mild |
| | 7 | 4.32 | Good, aromatic | 4.20 | Good, aromatic |
| | 14 | 4.25 | Good, aromatic | 4.12 | Good, aromatic |
| | 24 | 4.23 | Good, aromatic | 4.02 | Good, aromatic |
| 10 (I-1196) | 1 | 4.45 | Good, mild | 4.45 | Good, mild |
| | 7 | 4.43 | Good, mild | 4.32 | Good, aromatic |
| | 14 | 4.41 | Good, mild | 4.23 | Good, aromatic |
| | 24 | 4.34 | Good, mild | 4.23 | Good, aromatic |
| 11 | 1 | 4.50 | Good, | 4.50 | Good, |

TABLE 4-continued

| Ex. No. (CNCM No.) | Storage time (d) | Storage at 4° C. pH | Tasting | Storage at 12° C. pH | Tasting |
|---|---|---|---|---|---|
| (I-1198) | | | mild | | mild |
| | 7 | 4.38 | Good, mild | 4.29 | Good, aromatic |
| | 14 | 4.40 | Good, mild | 4.24 | Good, aromatic |
| | 24 | 4.35 | Mild, aromatic | 4.20 | Good, aromatic |

If these results are compared with one another and with those shown in Table 1, Example 1, it can be seen that the post-acidification of all these yogurts is very similar and far less rapid than that of the comparison yogurt (Table 1, Comparison Example i). This shows that the use of the selection process according to the invention enables mutants, particularly mutants having a DNA in which a fragment containing only part of the β-galactosidase gene is missing, to be selected from various mother strains, i.e. from any commercial "L. bulgaricus" strain. Used in combination with any commercial "S. thermophilis" strain, these mutants enable traditional yogurts having substantially the same remarkable keeping properties to be produced.

Examples 12–15 (selection)

The selection process according to the invention is used as described above to select a mutant of "L. bulgaricus" from four different commercial mother strains of which two have texturing, i.e. thickening, properties. Various mutants having a DNA in which a fragment containing at least part of the β-galactosidase gene and extending at least below that gene over at least 1.0 kb is missing are thus selected.

Of these mutants, four, namely one for each different mother strain, were lodged by way of example under the Budapest Treaty on 02.04.92 at the Collection Nationale de Cultures de Microorganismes (CNCM), Institut Pasteur, 28 rue du Dr. Roux, 7524 Paris Cedex 15, France, where they were given the numbers CNCM I-1192, I-1194, I-1195 and I-1197.

Details of the morphology and the properties of these strains are given in the following:

Morphology:

Gram-positive microorganisms, negative catalases, optional anaerobes.

Straight bacilli without flagella or spore formation.

Fermentation of sugars:

| | production of acid from: | | | |
|---|---|---|---|---|
| | I-1192 | I-1194 | I-1195 | I-1197 |
| D-Glucose | + | + | + | + |
| D-Fructose | + | + | + | + |
| D-Mannose | + | + | + | + |
| Trehalose | + | − | − | − |

Others:

No production of acid from lactose (no functional β-galactosidase enzyme).

The strains CNCM I-1195 and I-1197 have texturing properties (production of polysaccharides).

Examples 12–15 (production of yogurts)

Four starters each containing approximately $10^8$ cells/ml of one of the "L. bulgaricus" strains CNCM I-1192, I-1194, I-1195 and I-1197 and a starter containing approximately $10^9$ cells/ml of a commercial Streptococcus thermophilus culture are prepared.

Four batches of 40 l fresh milk containing 3.7% fats strengthened with 1.5% skimmed milk powder and pasteurized for 3 mins. at 98° C. are prepared and are each inoculated with 2% by volume of one of the four starters of "L. bulgaricus" CNCM I-1192, I-1194, I-1195 and I-1197. The batches are then incubated for 9 h at 40° C.

The yogurts obtained have a firm and smooth texture (I-1192, I-1194) or a creamy texture (I-1194, I-1195), a mild to very mild and typical flavour, respective pH values of 4.60 (I-1192), 4.80 (I-1194), 4.76 (I-1195) and 4.66 (I-1197) and respective contents, expressed as the number of cells of "L. bulgaricus" and "S. thermophilus" per ml, of $9.9 \cdot 10^6$ (I-1192) and $1.1 \cdot 10^8$, $3.5 \cdot 10^6$ (I-1194) and $7.9 \cdot 10^7$, $2.3 \cdot 10^8$ (I-1195) and $9.3 \cdot 10^7$ and $1.7 \cdot 10^7$ (I-1197) and $1.7 \cdot 10^8$.

These yogurts are subjected to the storage test described in Example 1. The results are set out in Table 5 below.

TABLE 5

| Ex. No. (CNCM No.) | Storage time (d) | Storage at 4° C. pH | Tasting | Storage at 12° C. pH | Tasting |
|---|---|---|---|---|---|
| 12 (I-1192) | 1 | 4.57 | Good, mild | 4.57 | Good, mild |
| | 7 | 4.46 | Good, mild | 4.33 | Good, aromatic |
| | 14 | 4.49 | Good, mild | 4.33 | Good, aromatic |
| | 24 | 4.40 | Good, aromatic | 4.26 | Good, aromatic |
| 13 (I-1194) | 1 | 4.90 | Very mild | 4.90 | Very mild |
| | 7 | 4.77 | Very mild | 4.60 | Good, mild |
| | 14 | 4.74 | Very mild | 4.64 | Good, mild |
| | 24 | 4.66 | Good, mild | 4.53 | Good, mild |
| 14 (I-1195) | 1 | 4.61 | Good, mild | 4.61 | Good, mild |
| | 7 | 4.57 | Good, mild | 4.43 | Good, mild |
| | 14 | 4.59 | Good, mild | 4.34 | Good, aromatic |
| | 24 | 4.49 | Good, mild | 4.29 | Good, aromatic |
| 15 (I-1196) | 1 | 4.52 | Good, mild | 4.52 | Good, mild |
| | 7 | 4.48 | Good, mild | 4.34 | Good, aromatic |
| | 14 | 4.41 | Good, mild | 4.18 | Good, aromatic |
| | 24 | 4.31 | Mild, aromatic | 4.20 | Good, aromatic |

If these results are compared with one another and with those shown in Table 1, Example 2, it can be seen that the post-acidification of all these yogurts is very similar, far less rapid than that of the comparison yogurt (Table 1, Comparison Example i) and even lower than that of the yogurts of Examples 1, 8, 9, 10 and 11. This shows that the use of the selection process according to the invention enables mutants, particularly mutants having a DNA in which a fragment containing at least part of the β-galactosidase gene and extending at least below that gene over at least 1.0 kb is missing, to be selected from various mother strains, i.e. from any commercially available L. bulgaricus strain. Used in combination with any commercial S. thermophilus strain, these mutants enable traditional yogurts having substantially the same remarkable keeping properties to be produced.

We claim:

1. A process for preparing a yogurt comprising inoculating and fermenting a milk with a strain of Streptococcus thermophilus and a lac(−) mutant strain of Lactobacillus bulgaricus, wherein the DNA of the mutant strain has a deletion of at least part of the β-galactosidase gene.

2. A process according to claim 1 wherein the DNA deletion is contained within the β-galactosidase gene of the mutant Lactobacillus bulgaricus.

3. A process according to claim 1 wherein the DNA deletion extends from within to at least 1 kb downstream of the β-galactosidase gene of the mutant Lactobacillus bulgaricus.

4. A process according to claim 1 wherein the milk to be inoculated does not contain supplemented glucose.

5. A process according to claim 2 wherein the milk to be inoculated does not contain supplemented glucose.

6. A process according to claim 3 wherein the milk to be inoculated does not contain supplemented glucose.

7. A process according to claim 1 wherein the milk is inoculated with 0.2% to 5% by volume of a culture containing $10^6$ to $10^{10}$ cells/ml of Lactobacillus bulgaricus mutant and with 1% to 5% by volume of a culture containing $10^6$ to $10^{10}$ cells/ml Streptococcus thermophilus.

8. A process according to claim 1 wherein the milk is inoculated with 0.5% to 3% by volume of a culture containing $10^8$ to $10^9$ cells/ml of Lactobacillus bulgaricus mutant and with 2% to 4% by volume of a culture containing $10^8$ to $10^9$ cells/ml Streptococcus thermophilus.

9. A process according to claim 1 wherein a milk containing 10% to 20% dry matter is inoculated and fermented for from 2.5 hours to 15 hours at from 35° C. to 48° C.

10. A process according to claim 1 wherein the mutant Lactobacillus bulgaricus is strain CNCM I-1067.

11. A process according to claim 1 wherein the mutant Lactobacillus bulgaricus is strain CNCM I-1068.

12. A process according to claim 1 wherein the mutant Lactobacillus bulgaricus is strain CNCM I-1191.

13. A process according to claim 1 wherein the mutant Lactobacillus bulgaricus is strain CNCM I-1192.

14. A process according to claim 1 wherein the mutant Lactobacillus bulgaricus is strain CNCM I-1193.

15. A process according to claim 1 wherein the mutant Lactobacillus bulgaricus is strain CNCM I-1194.

16. A process according to claim 1 wherein the mutant Lactobacillus bulgaricus is strain CNCM I-1195.

17. A process according to claim 1 wherein the mutant Lactobacillus bulgaricus is strain CNCM I-1196.

18. A process according to claim 1 wherein the mutant Lactobacillus bulgaricus is strain CNCM I-1197.

19. A process according to claim 1 wherein the mutant Lactobacillus bulgaricus is strain CNCM I-1198.

* * * * *